United States Patent [19]

Boris et al.

[11] Patent Number: 4,595,689

[45] Date of Patent: Jun. 17, 1986

[54] 4-(8-BROMODIBENZ[B,F]OXEPIN-10-YL)-1,2,3,6-TETRAHYDRO-1-METHYLPYRIDINE AND 4-(2-BROMODIBENZO[A,D]CYCLOPHETA-TRIENE-11-YL)-1,2,3,6-TETRAHYDRO-1-METHYLPYRIDINE FOR DERMAL INFLAMMATION

[75] Inventors: Alfred Boris, Parsipanny; Robert W. Guthrie, Saddle Brook; Richard W. Kierstead, North Caldwell, all of N.J.

[73] Assignee: Hoffmann-LaRoche Inc., Nutley, N.J.

[21] Appl. No.: 578,726

[22] Filed: Feb. 9, 1984

[51] Int. Cl.$^4$ .......................................... C07D 407/04
[52] U.S. Cl. .................................. 514/337; 514/277; 546/269; 546/285
[58] Field of Search ................ 546/269, 285; 424/263; 514/337, 277

[56] References Cited

U.S. PATENT DOCUMENTS 3,479,356  11/1969  Fouche et al. ...................... 546/285

OTHER PUBLICATIONS

Fouche, C.A. 77811t, vol. 70, 1969.
Societe et al., C.A. 81186f, vol. 71, 1969.
Fouche, C.A. 70656u, vol. 80, 1974 and C.A. 66848a, vol. 72, 1970.
Societe, C.A. 5738e, vol. 75, 1971.

Primary Examiner—Jane T. Fan

Attorney, Agent, or Firm—Jon S. Saxe; Bernard S. Leon; Matthew Boxer

[57] ABSTRACT

A method of treating inflammation which comprises topically administering to the affected area a compound of the formula

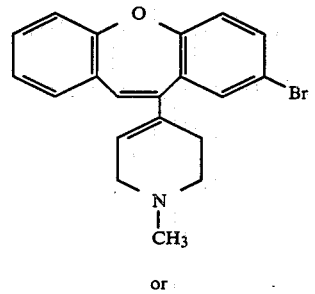

or

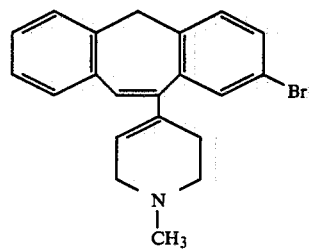

or a pharmaceutically acceptable addition salt thereof, is described.

4 Claims, No Drawings

4-(8-BROMODIBENZ[B,F]OXEPIN-10-YL)-1,2,3,6-TETRAHYDRO-1-METHYLPYRIDINE AND 4-(2-BROMODIBENZO[A,D]CYCLOPHETATRIENE-11-YL)-1,2,3,6-TETRAHYDRO-1-METHYLPYRIDINE FOR DERMAL INFLAMMATION

BACKGROUND OF THE INVENTION

The invention relates to a compound, pharmaceutical compositions and methods for the treatment of inflammation of dermal tissues. Conditions which can be treated are for example dermatitis of varying etiology and keratosis. Among the more common conditions which can be treated, as described herein, are inflammation occurring in psoriasis and eczema.

In the past, the most widely used compositions for the treatment of topical inflammation contained corticosteroids particularly hydrocortisone. While the corticosteroids are effective in reducing the inflammation and associated symptoms, they have undesirable side effects, especially when their use is prolonged. Among the effects associated with prolonged use of corticosteroids are thinning and striation of the skin and interference with the body's immune system. Because of these undesirable side effects, the art has been searching for a nonsteroidal pharmaceutical agent having topical anti-inflammatory activity comparable to the corticosteroids but without the concomitant undesirable side effects. The present invention provides for compositions containing non-steroidal, topical, anti-inflammatory agents and their use as topical anti-inflammatories.

SUMMARY OF THE INVENTION

The invention, relates to compounds used in the treatment of inflammation. The compounds are 4-(8-bromodibenz[b,f]oxepin-10-yl)-1,2,3,6-tetrahydro-1-methylpyridine of the structure:

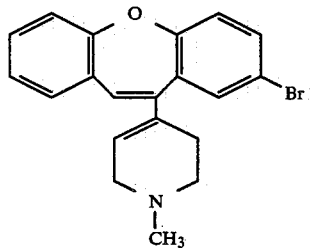

and 4-(2-bromodibenzo[a,d]cycloheptatriene-11-yl)-1,2,3,6-tetrahydro-1-methylpyridine of the structure:

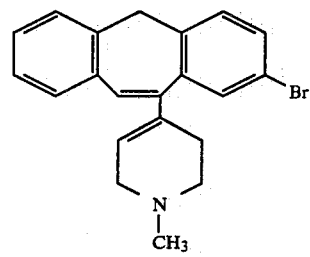

A process for the preparation of 4-(8-bromodibenz[b,f]oxepin-10-yl)-1,2,3,6-tetrahydro-1-methylpyridine is provided. In another aspect the invention relates to compositions for treating inflammation containing effective amounts of either of the above two compounds in a pharmaceutically acceptable carrier material for topical application. Methods for treating inflammation comprise topically administering an effective amount of a composition containing either of the above two compounds or pharmaceutically acceptable addition salts thereof in a pharmaceutically acceptable carrier material.

DETAILED DESCRIPTION OF THE INVENTION

As used herein the term "n-alkyl" denotes a straight chain alkyl having one to seven carbon atoms.

This invention relates to compositions, a method for treating topical inflammation, and 4-(8-bromodibenz[b,f]oxepin-10-yl)-1,2,3,6-tetrahydro-1-methylpyridine. The compositions contain 4-(8-bromodibenz[b,f]oxepin-10-yl)-1,2,3,6-tetrahydro-1-methylpyridine or 4-(2-bromodibenzo[a,d]cycloheptatrine-11-yl)-1,2,3,6-tetrahydro-1-methylpyridine, and an inert pharmaceutical carrier. 4-(2-Bromodibenzo[a,d]cycloheptatriene-11-yl)-1,2,3,6-tetrahydro-1-methylpyridine, is a known compound. Its preparation is described in U.S. Pat. No. 3,479,356.

The 4-(8-bromodibenz[b,f]oxepin-10-yl)-1,2,3,6-tetrahydro-1-methylpyridine, which is the compound of formula VI, can be prepared according to Reaction Scheme I below:

Reaction Scheme I

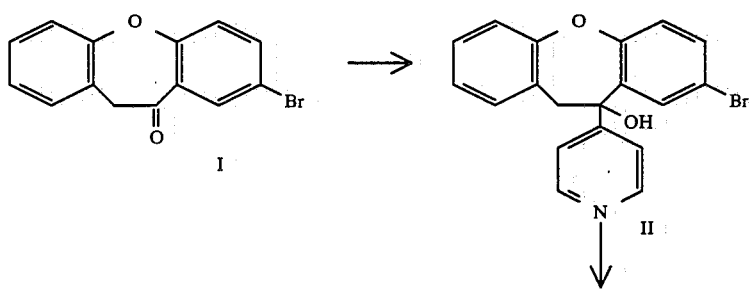

Reaction Scheme I

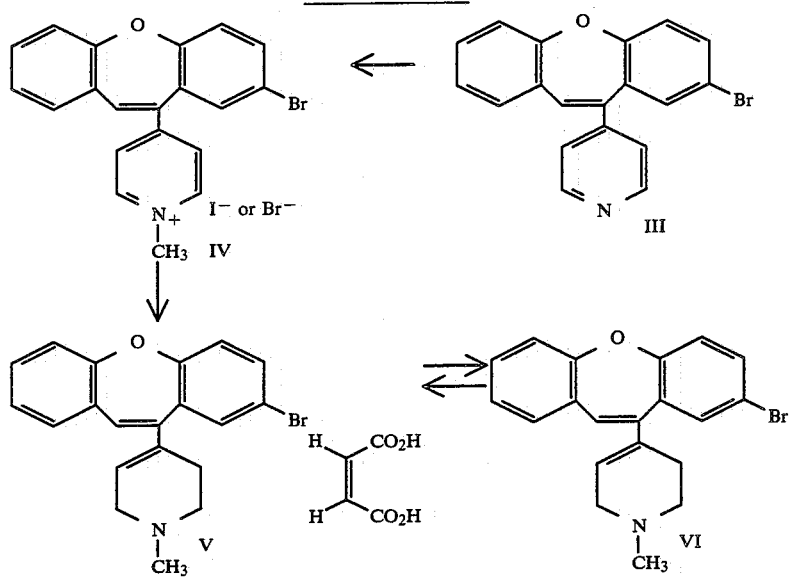

-continued

The compound of formula I, 8-bromodibenz-[b,f]oxepin-10-one is a known compound. See, I. Ueda et al, *Chem. Pharm. Bull.*, 1975 23 (10), 2223.

The compound of formula I is converted to the compound of formula II by reacting the former with 4-lithiopyridine. A stirred and chilled suspension of the compound of Formula I is prepared. The solvent used is a polar, aprotic solvent such as tetrahydrofuran, 1,2-dimethoxyethane, or most preferably anhydrous ether. The temperature of the suspension is about −40° to about −45° C. To the suspension is slowly added a mixture of 4-lithiopyridine whose preparation is described below. After addition, the resulting mixture is stirred at a temperature of about −78° to 0° or, more preferably at about −45°, for a period of about 10 minutes to an hour or, more preferably, about 30 minutes, and then allowed to warm up to about room temperature.

The compound of formula II, which is 8-bromo-10,11-dihydro-10-(4-pyridinyl)dibenz[b,f]oxepin-10-ol, is recovered and isolated from the reaction mixture by known methods, for example, precipitation or the like.

The compound of formula II is converted to the compound of formula III, which is 4-(8-bromodibenz[b,f]oxepin-10-yl)pyridine, by heating at reflux a mixture of the former in an acid such as aqueous methanesulfonic acid or, more preferably, trifluoracetic acid, for about one to eight hours, more preferably, for five hours.

The compound of formula III is converted to a salt of formula IV by reacting the former with methyl iodide or methyl bromide in a polar solvent at reflux. The polar solvent can be methanol, acetone or, most preferably, acetonitrile. Refluxing is continued for about 30 minutes to about two hours or, more preferably, about ninety minutes. The reaction mixture is then cooled. The resulting crystalline material is filtered off and washed to give a salt of formula IV, that is, 4-(8-bromodibenz[b,f]-oxepin-10-yl)-1-methylpyridinium iodide or bromide.

A salt of formula IV is converted to the salt of formula V, by reducing a stirred suspension of the former in ethanol or more preferably methanol with potassium borohydride or, more preferably, sodium borohydride and water. This reduction reaction is conducted at about 0° C. to about room temperature, or more preferably at 0° to 5°. The resulting product is then treated with a methanolic or ethanolic solution of maleic acid to yield the salt of formula V, which is 4-(8-bromodibenz[b,f]oxepin-10-yl)-1,2,3,6-tetrahydro-1-methylpyridine, (Z)-2-butenedioate (1:1) salt.

The salt of formula V is converted to the compound of formula VI, by partitioning the former between an excess of a basic solution, such as a sodium hydroxide, a sodium bicarbonate or a potassium carbonate solution and dichloromethane and drying and evaporating the dichloromethane phase. The residue is crystallized from ethyl acetate or a dichloromethane-ether mixture to yield the compound of formula VI, which is 4-(8-bromodibenz[b,f]oxepin-10-yl)-1,2,3,6-tetrahydro-1-methylpyridine.

4-Lithiopyridine which is used in the conversion of the compound of formula I to the compound of formula II is prepared as follows. Under an inert atmosphere of nitrogen or, more preferably, argon, a solution of 4-bromopyridine in a polar, aprotic solvent, such as tetrahydrofuran or 1,2-dimethoxyethane or more preferably anhydrous ether, is cooled to a temperature in the range of from about −78° to about 0°, more preferably at about −78° C. This solution is transferred slowly to a stirred solution of n-alkyl lithium, most preferably b-butyl lithium, in pentane or, more preferably, hexane. The resulting mixture is stirred from about 10 minutes to about an hour or, more preferably for about 20 minutes, while the temperature is maintained at about −45° to about −40°. The 4-lithiopyridine thus formed is used without being separated from its reaction mixture in the converson of the compound of formula I to the compound of formula II.

The 4-(8-bromodibenz[b,f]oxepin-10-yl)-1,2,3,6-tetrahydro-1-methylpyridine of the invention forms acid addition salts with conventional pharmaceutically acceptable acids, that is, inorganic acids such as hydrochloric acid, sulfuric acid, phosphoric acid, hydrobromic acid and the like, or organic acids such as citric acid, acetic acid, succinic acid, maleic acid, methanesulfonic acid, p-toluenesulfonic acid and the like.

In accordance with the method of the invention, a composition comprising 4-(8-bromodibenz[b,f]oxepin-10-yl)-1,2,3,6-tetrahydro-1-methylpyridine or 4-(2-bromodibenzo[a,d]cycloheptatriene-11-yl)-1,2,3,6-tetrahydro-1-methylpyridine and an inert pharmaceutical carrier material for topical application, is applied topically to the inflamed dermal tissues of the warm blooded animal to be treated. Either of the compounds can be conveniently applied in an effective amount of that compound or pharmaceutically acceptable salts thereof. Topical dosage forms of the compositions of the invention will preferably contain from about 0.01 to 10 weight percent, most preferably from 0.1 to 1.0 weight percent of either the compounds of the invention or pharmaceutically acceptable salts thereof, based on the total weight of the composition. The minimum amount of either of the compounds of the invention which is effective may vary somewhat among hosts and depending on which compound of the invention is employed. However, it is well within the skill of the practitioner to determine the effective amount in any particular circumstance. By "effective amount" is meant an amount which is sufficient to reduce the symptoms of the inflammation, for example, to lessen redness, scaling, itching and pain or to reduce thickening of the skin at the site of the inflammation. Preferably, the topical composition will be applied in a thin layer to the inflamed area from one to six times daily, depending on factors such as the severity and type of condition being treated, the location of the inflamed area being treated and the concentration of active ingredient in the topical composition.

The term "topical" as employed herein relates to the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing either of the compounds with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous linings of the mouth or lower colon.

Ointments and creams encompass formulations having oleaginous, adsorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like: gelatin or gums, which incorporate the active ingredient in a vehicle made up of water, alcohol, glycerin, and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

Aerosols are made up of solutions or suspensions of active ingredients in an inert carrier which are dispensed with the use of a special spraying device. Some of the carriers commonly used are trichloromonofluoromethane and dichlorodifluoromethane.

The pharmaceutical compositions of the invention can be exposed to conventional pharmaceutical expedients such as sterilization and/or can contain conventional pharmaceutical additives such as preservatives, stabilizing agents, wetting agents, emulsifying agents, salts for adjusting the osmotic pressure, buffers and the like. If desired, they can also contain other therapeutically useful materials including ingredients known to have topical anti-inflammatory activity, in conjunction with the compounds utilized in the compositions of the invention. These ingredients are employed in the known effective concentrations.

Table I sets forth the topical anti-inflammatory activity of compounds utilized in the compositions and method of the invention.

The following test procedures were used to demonstrate the topical anti-inflammatory activity of the compounds listed in Table I.

CANTHARIDIN INDUCED INFLAMMATION IN THE RAT

A solvent vehicle was prepared which was used to apply cantharidin or cantharidin and test compound to rats. The solvent vehicle was a solution of 1 part ethanol, 1.5 parts collodion, 2 parts acetone and 3 parts diethylether. When it was desired to apply cantharidin to rats, cantharidin was added to the solvent vehicle in such an amount that there were 400 $\mu$g of cantharidin in 0.1 ml of solvent vehicle. When it was desired to apply cantharidin and test compound to rats, cantharidin and test compound were added to the solvent vehicle in such amounts that there were both 400 $\mu$g of cantharidin and 100 $\mu$g of test compound in 0.1 ml of solvent vehicle. Cantharidin or cantharidin plus the test compound at a dose of 100 $\mu$g were applied topically to the outer surface of the ears of Charles River CD 21-day-old male rats in a volume of 0.1 ml of solvent vehicle described above. Separate groups of rats were treated with solvent vehicle alone, cantharidin alone, and cantharidin plus test compound. Autopsy was carried out 72 hours after cantharidin administration. Uniform punches were obtained through the site of application and weighed. Weight changes reflect effects on both the fluid and tissue components of the inflammatory process. A reduction in weight of the skin punch taken from rats treated with irritant plus test compound, compared with those of rats treated with irritant alone, indicates anti-inflammatory activity. (*J. Invest. Dermatol.* 68, 161–164, 1977).

TABLE I

| Topical Activity in the Cantharidin Rat Test | | |
|---|---|---|
| Compound | Topical Dose ($\mu$g) | % Inhibition of Inflammation |
| 4-(8-Bromodibenz[b,f]oxepin-10-yl),1,2,3,6-tetrahydro-1-methylpyridine | 100 | 36 |
| 4-(2-Bromodibenzo[a,d]cycloheptatriene-11-yl)-1,2,3,6-tetrahydro-1-methylpyridine | 100 | 37 |

The following Examples further illustrate the invention. All parts and percentages are by weight and all temperatures are in degrees Centigrade, unless otherwise stated.

EXAMPLE 1

8-Bromo-10,11-dihydro-10-(4-pyridinyl)dibenz[b,f]oxepin-10-ol (Compound II)

Under an argon atmosphere, a solution of 4-bromopyridine (16.6 g) in anhydrous ether (90 ml) previously cooled to −40°, was transferred slowly via a cannular to a stirred solution of n-butyl lithium in hexane (1.55M; 68 ml) cooled to −78°. The mixture was stirred at −78° for 20 minutes and the resulting 4-lithiopyridine was transferred to a chilled (−78°) stirred suspension of 8-bromodibenz[b,f]oxepin-10(11H)-one (15 g) in anhydrous ether (100 ml). The reaction was stirred at −78° for 30 minutes, then the cooling bath was removed and the mixture was treated with 100 ml of water and allowed to warm to room temperature. The solids were filtered off, washed with water and dried to give 5.0 g of 8-bromo-10,11-dihydro-10-(4-pyridinyl)dibenz[b,f]oxepin-10-ol. The mother liquor was worked up and a total of 9.4 grams of the starting ketone 8-bromodibenz[b,f]oxepin-10(11H)-one were recovered.

A sample of 8-bromo-10,11-dihydro-10-(4-pyridinyl)-dibenz[b,f]oxepin-10-ol was crystallized from dichloromethane ether to afford an analytically pure material, mp 232°–233.5°.

EXAMPLE 2

4-(8-Bromodibenz[b,f]oxepin-10-yl)pyridine (Compound III)

A mixture of 8-bromo-10,11-dihydro-10-(4-pyridinyl)dibenz[b,f]oxepin-10-ol (3.0 g) in trifluoroacetic acid (18 ml) was heated at reflux under argon for five hours. The reaction mixture was concentrated to dryness in vacuo and the residual material was triturated using 1N sodium hydroxide aqueous solution (40 ml). The solids that formed were filtered off, washed thoroughly with water and the dried material was crystallized from dichloromethane-methanol. After the mixture was cooled overnight at 0°–5°, the solids were recovered by filtration, washed well with cold methanol to give 2.1 g of 4-(8-bromodibenz[b,f]oxepin-10-yl)pyridine, mp 195°–197°.

A sample of 4-(8-bromodibenz[b,f]oxepin-10-yl)pyridine was recrystallized from methanol to furnish an analytically pure specimen, mp 198°–199°.

EXAMPLE 3

4-(8-Bromodibenz[b,f]oxepin-10-yl)-1-methylpyridinium iodide (Salt IV)

A mixture of 4-(8-bromodibenz[b,f]oxepin-10-yl)pyridine (2.0 g) in acetonitrile (30 ml) containing methyl iodide (1.1 ml) was stirred under reflux in an argon atmosphere for ninety minutes. During this time the starting material gradually dissolved and a yellow solid began to precipitate from solution. The mixture was cooled to −10° and the solids were collected by filtration and were washed in turn with cold acetonitrile and ether to give 2.7 g of 4-(8-bromo-dibenz[b,f]oxepin-10-yl)-1-methylpyridinium iodide.

EXAMPLE 4

4-(8-Bromodibenz[b,f]oxepin-10-yl)-1,2,3,6-tetrahydro-1-methylpyridine,(Z)-2-butenedioate (1:1) salt (Salt V)

A stirred suspension of 4-(8-bromodibenz[b,f]oxepin-10-yl)-1-methylpyridinium iodide (2.7 g) in methanol (50 ml) was treated with sodium borohydride (1.04 g) and 15 ml of water. The mixture was stirred at ambient temperature for thirty minutes and then was diluted with 175 ml of water. The resulting solid was filtered off, washed with water and then was dissolved in dichloromethane (100 ml). The organic solution was washed with water, then was dried (potassium carbonate) and evaporated in vacuo. A solution of the residual solid in ethyl acetate (75 ml) was treated with a solution of maleic acid (0.64 g) in ethanol (5 ml). The crystalline product was recovered in two crops to give a total yield of 2.0 g of 4-(8-bromodibenz[b,f]oxepin-10-yl)-1,2,3,6-tetrahydro-1-methylpyridine, (Z)-2-butenedioate (1:1) salt, mp 186°–188°.

A small sample was recrystallized from methanol-ethyl acetate to give an analytically pure sample, mp 187°–188°.

EXAMPLE 5

4-(8-Bromodibenz[b,f]oxepin-10-yl)-1,2,3,6-tetrahydro-1-methylpyridine (Compound VI)

A portion of 4-(8-bromodibenz[b,f]oxepin-10-yl)-1,2,3,6-tetrahydro-1-methylpyridine, (Z)-2-butenedioate (1:1) salt (1.0 g) was partitioned between 1N aqueous sodium hydroxide solution (50 ml) and dichloromethane (50 ml). After all the solid material had dissolved, the layers were separated and the dichloromethane phase was dried (potassium carbonate) and evaporated in vacuo. The residual solid was crystallized from dichloromethane-ether to furnish 550 mg of 4-(8-bromodibenz[b,f]oxepin-10-yl)-1,2,3,6-tetrahydro-1-methylpyridine mp 144°–145.5°.

EXAMPLE 6

A cream containing the following ingredients can be produced in a conventional manner:

| Ingredient | % w/w |
|---|---|
| 4-(8-Bromodibenz[b,f]oxepin-10-yl)-1,2,3,6-tetrahydro-1-methylpyridine | 0.1–1.00 |
| Glyceryl monostearate S.E. | 10.00 |
| Cetyl alcohol | 2.00 |
| Petrolatum | 5.00 |
| Methyl paraben | 0.15 |
| Propyl paraben | 0.05 |
| Propylene glycol | 20.00 |
| Water to | 100.00 |

In a similar manner, creams may be prepared by substituting 4-(2-bromodibenzo[a,d]cycloheptatriene-11-yl)-1,2,3,6-tetrahydro-1-methylpyridine at equal concentrations, for the 8-bromodibenz[b,f]oxepin-10-yl)1,2,3,6-tetrahydro-1-methylpyridine in the composition described above.

EXAMPLE 7

A lotion containing the following ingredients can be produced in a conventional manner:

| Ingredient | % w/w |
| --- | --- |
| 4-(8-Bromodibenz[b,f]oxepin-10-yl)1,2,3,6-tetrahydro-1-methylpyridine | 0.1–1.00 |
| Cetearyl alcohol and ceteareth-20 | 2.00 |
| Glyceryl monostearate | 4.00 |
| Isopropyl myristate | 10.00 |
| Ceteth-20 | 5.00 |
| Cetyl alcohol | 2.00 |
| Dehydroacetic acid | 0.1 |
| Imidizolidinyl urea | 0.5 |
| Xanthan gum | 0.5 |
| Polyethylene glycol 400 | 5.00 |
| Water to | 100.00 |

In a similar manner, lotions may be prepared by substituting 4-(2-bromodibenzo[a,d]cycloheptatriene-11-yl)-1,2,3,6-tetrahydro-1-methylpyridine at equal concentrations, for the 4-(8-bromodibenz[b,f]oxepin-10-yl)-1,2,3,6-tetrahydro-1-methylpyridine in the composition described above.

EXAMPLE 8

An ointment containing the following ingredients can be prepared in a conventional manner:

| Ingredient | % w/w |
| --- | --- |
| 4-(8-Bromodibenz[b,f]oxepin-10-yl)1,2,3,6-tetrahydro-1-methylpyridine | 0.1–1.00 |
| Hydrogenated Lanolin | 20.00 |
| Propylene glycol | 20.00 |
| Mineral oil | 10.00 |
| Microcrystalline wax | 2.50 |
| Petrolatum to | 100.00 |

In a similar manner, ointments may be prepared by substituting 4-(2-bromodibenzo[a,d]cycloheptatriene-11-yl)-1,2,3,6-tetrahydro-1-methylpyridine at equal concentrations, for the 4-(8-bromodibenz[b,f]oxepin-10-yl)-1,2,3,6-tetrahydro-1-methylpyridine in the composition described above.

We claim:

1. A method for treating dermal inflammation which comprises topically administering to the affected area an effective amount of a compound selected from the group consisting of 4-(8-bromodibenz[b,f]oxepin-10-yl)-1,2,3,6-tetrahydro-1-methylpyridine, 4-(2-bromodibenzo[a,d]cycloheptatriene-11-yl)-1,2,3,6-tetrahydro-1-methylpyridine or a pharmaceutically acceptable addition salt thereof.

2. The method in accordance with claim 1, wherein the compound is 4-(2-bromodibenzo[a,d]cycloheptatriene-11-yl)-1,2,3,6-tetrahydro-1-methylpyridine.

3. The method in accordance with claim 1 wherein the compound is 4-(8-bromodibenz[b,f]oxepin-10-yl)-1,2,3,6-tetrahydro-1-methylpyridine.

4. The method in accordance with claim 1, wherein the pharmaceutically acceptable addition salt is 4-(8-bromodibenz[b,f]oxepin-10-yl)-1,2,3,6-tetrahydro-1-methylpyridine, (Z)-2-butenedioate (1:1) salt.

* * * * *